(12) United States Patent
Ramadhyani et al.

(10) Patent No.: US 12,390,260 B2
(45) Date of Patent: *Aug. 19, 2025

(54) FLEXIBLE CRYOPROBE

(71) Applicant: Biocompatibles UK Limited, Camberley (GB)

(72) Inventors: Satish Ramadhyani, Minneapolis, MN (US); Graig Kveen, Maple Grove, MN (US); Harishankar Natesan, Minneapolis, MN (US)

(73) Assignee: Biocompatibles UK Limited, Camberley (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/750,426

(22) Filed: Jun. 21, 2024

(65) Prior Publication Data
US 2024/0335223 A1    Oct. 10, 2024

Related U.S. Application Data

(63) Continuation of application No. 16/994,145, filed on Aug. 14, 2020, now Pat. No. 12,016,608.
(Continued)

(51) Int. Cl.
*A61B 18/02* (2006.01)
*A61B 18/00* (2006.01)

(52) U.S. Cl.
CPC .... *A61B 18/02* (2013.01); *A61B 2018/00017* (2013.01); *A61B 2018/00583* (2013.01); *A61B 2018/0262* (2013.01)

(58) Field of Classification Search
CPC .......... A61B 18/02; A61B 2018/00017; A61B 2018/00583; A61B 2018/0262
See application file for complete search history.

(56) References Cited

U.S. PATENT DOCUMENTS

| 5,520,682 A | 5/1996 | Baust et al. |
| 9,439,709 B2 | 9/2016 | Duong et al. |
| (Continued) | | |

FOREIGN PATENT DOCUMENTS

| CN | 107049467 | 8/2017 |
| CN | 210019628 | 2/2020 |
| (Continued) | | |

OTHER PUBLICATIONS

"Communication pursuant to Article 94(3) EPC," for European Patent Application No. 20761720.0 mailed Jan. 2, 2025 (5 pages).
(Continued)

*Primary Examiner* — Linda C Dvorak
*Assistant Examiner* — Abigail Bock
(74) *Attorney, Agent, or Firm* — Pauly, DeVries Smith & Deffner LLC

(57) ABSTRACT

A cryoablation tool may include a catheter. The catheter may have a shaft having: a proximal end, a distal end, a shaft wall extending between the proximal end and the distal end, the shaft wall having an outer surface and an inner surface and a vacuum gap defined therebetween that forms a vacuum chamber, the inner surface of the shaft wall being gas permeable, a shaft lumen bounded by the inner surface of the shaft wall, the shaft lumen for carrying a cryogen gas, and the vacuum chamber having a proximal opening connectable to a vacuum source, the proximal opening establishing vacuum communication between the vacuum chamber and the vacuum source.

20 Claims, 5 Drawing Sheets

Related U.S. Application Data

(60) Provisional application No. 62/886,858, filed on Aug. 14, 2019.

(56) References Cited

U.S. PATENT DOCUMENTS

| | | | |
|---|---|---|---|
| 10,166,367 | B2 | 1/2019 | Tegg et al. |
| 10,905,490 | B2 | 2/2021 | Clark et al. |
| 11,786,285 | B2 | 10/2023 | Ramadhyani et al. |
| 12,016,608 | B2 * | 6/2024 | Ramadhyani .......... A61B 18/02 |
| 12,156,687 | B2 | 12/2024 | Brodbeck et al. |
| 2003/0060815 | A1 | 3/2003 | Lalonde et al. |
| 2008/0027422 | A1 | 1/2008 | Vancelette et al. |
| 2008/0147055 | A1 | 6/2008 | Duong et al. |
| 2010/0076421 | A1 | 3/2010 | Baust et al. |
| 2014/0039476 | A1 | 2/2014 | Duong et al. |
| 2015/0216581 | A1 | 8/2015 | Duong et al. |
| 2018/0146999 | A1 | 5/2018 | Baust |
| 2021/0045793 | A1 | 2/2021 | Ramadhyani et al. |
| 2021/0045794 | A1 | 2/2021 | Ramadhyani et al. |
| 2024/0397255 | A1 | 11/2024 | Nagaoka |
| 2024/0423688 | A1 | 12/2024 | True et al. |
| 2024/0423689 | A1 | 12/2024 | True et al. |
| 2025/0082385 | A1 | 3/2025 | True et al. |

FOREIGN PATENT DOCUMENTS

| | | |
|---|---|---|
| DE | 1953834 | 5/1971 |
| WO | 9204872 | 4/1992 |
| WO | 9957494 | 11/1999 |
| WO | 2006006990 | 1/2006 |
| WO | 2018087563 | 5/2018 |
| WO | 2024243440 | 11/2024 |
| WO | 2024243447 | 11/2024 |

OTHER PUBLICATIONS

"Decision of Rejection," for Japanese Patent Application No. 2022-508910 mailed Jun. 4, 2024 (5 pages) with English translation.

"First Office Action," for Chinese Patent Application No. 202080071564.8 mailed Oct. 18, 2024 (16 pages) with English summary.

"International Search Report and Written Opinion," received for PCT Patent Application No. PCT/US2020/046474, mailed on Nov. 20, 2020, 12 pages.

"Notice of Allowance," for U.S. Appl. No. 16/994,145 mailed Feb. 21, 2024 (11 pages).

"Office Action," for Israeli Patent Application No. 290629 mailed Sep. 12, 2024 (3 pages) no English translation.

"Response to Examination Report," for Australian Patent Application No. 2020330099 filed Dec. 22, 2023 (19 pages).

"Response to Non Final Office Action," for U.S. Appl. No. 16/994,145, filed Jan. 9, 2024 (12 pages).

"Response to," First Office Action for Israeli Patent Application No. 290629 filed Dec. 8, 2024, 11 pages, with English summary.

"Second Office Action," for JP Patent Application No. 2022-508910 mailed Dec. 12, 2023 (7 pages).

"First Examination Report," for Australian Patent Application No. 2024202153 mailed Feb. 27, 2025 (4 pages).

"International Search Report & Written Opinion," for PCT Patent Application No. PCT/US2024/030844 mailed Sep. 10, 2024 (11 pages).

"International Search Report and Written Opinion," for PCT Patent Application No. PCT/US2024/030857 mailed Dec. 9, 2024 (17 pages).

"International Search Report and Written Opinion," for PCT Patent Application No. PCT/US2024/030864 mailed Sep. 16, 2024 (35 pages).

"Invitation to Pay Additional Fees and, Where Applicable, Protest Fee," for PCT Patent Application No. PCT/US2024/030857 mailed Oct. 15, 2024 (13 pages).

"Response to First Examination Report," for Australian Patent Application No. 2024202153 filed Mar. 25, 2025 (12 pages).

"Office Action," for Japanese Patent Application No. 2024-164825 mailed May 7, 2025 (13 pages) with English translation.

"Response to Communication pursuant to Article 94(3) EPC," for European Patent Application No. 20761720.0 filed Apr. 23, 2025 (15 pages).

* cited by examiner

FLEXIBLE CRYOPROBE

CROSS REFERENCE TO RELATED APPLICATION

This application is a Continuation of U.S. patent application Ser. No. 16/994,145, filed Aug. 14, 2020, now U.S. Pat. No. 12,016,608 which claims priority to Provisional Application No. 62/886,858, filed Aug. 14, 2019, which is herein incorporated by reference in its entirety.

BACKGROUND OF THE INVENTION

This disclosure relates to a cryoprobe for use in cryoablation and a system for cryoablation.

During cryosurgery, a surgeon may deploy one or more cryoprobes to ablate a target area of a patient anatomy by freezing and thawing the tissue. In one example, a cryoprobe uses the Joule-Thomson effect to produce cooling or heating of the probe tip. In such cases, the expansion of a cryofluid in the cryoprobe from a higher pressure to a lower pressure leads to cooling of the device tip to temperatures at or below those corresponding to cryoablating a tissue in the vicinity of the tip. Heat transfer between the expanded cryofluid and the outer walls of the cryoprobe leads to formation of an ice ball, in the tissue around the tip and consequent cryoablation the tissue.

Some cryoprobes may be useful for ablating lesions in a human lung. In such cases, the cryoprobes may have to navigate tortuous passageways. Cryoprobes with rigid shafts may not be suitable for such applications.

SUMMARY OF THE INVENTION

In general, various embodiments relating to devices, systems, and methods for a cryoprobe, an insulated sheath, and an insulated catheter. Such devices, systems, and methods can be used in an exemplary application in medical technology. These embodiments can be useful in such an exemplary application, for instance, when providing cryoablation. Yet, at the same time, these embodiments may solve some of the problems noted above.

One aspect of the invention relates to a cryoablation tool comprising a shaft. The shaft may comprise a proximal end, a distal end, a shaft wall. The shaft wall may extend between the proximal end and the distal end and also have an outer surface, an inner surface, and a gap defined there-between that forms a chamber. In some aspects the shaft wall can be gas permeable. The shaft may further comprise a shaft lumen bounded by the inner surface of the shaft wall as well as a cryogen supply conduit. The cryogen supply conduit may be housed within the shaft lumen and may be further configured to carry a cryogen from a cryogen source to a distal portion of the cryoablation tool. The shaft lumen may additionally provide a return flow passage configured to carry the cryogen gas away from the distal end of the cryoablation tool. The chamber, defined between the outer surface and the inner surface of the shaft wall, may have a proximal opening connectable to a vacuum source. The proximal opening may establish vacuum communication between the chamber and the vacuum source. The chamber may also have a chamber fluid pressure therein and the chamber fluid pressure may regulatable via the vacuum source.

Another aspect of the invention relates to an insulated sheath suitable for use with a cryoablation tool. The sheath may comprise a shaft having a proximal end, a distal end, and a shaft wall. The shaft wall may extend between the proximal end and the distal end and also have an outer surface, an inner surface, and a gap defined there-between that forms a chamber. In some aspects the shaft wall can be gas permeable. The shaft may further comprise a shaft lumen bounded by the inner surface of the shaft wall. The shaft lumen may be configured for receiving a cryoablation tool and may also be open at the proximal end and the distal end. The chamber, defined between the outer surface and the inner surface of the shaft wall, may be sealed at the distal end and have a proximal opening connectable to a vacuum source. The proximal opening may be used to establish vacuum communication between the chamber and the vacuum source. The chamber may also have a chamber fluid pressure therein and the chamber fluid pressure may regulatable via the vacuum source.

An additional aspect of the invention relates to an insulated catheter. The insulated catheter may comprise a tubular shaft having a proximal end, a distal end, and a shaft wall. The shaft wall may extend between the proximal end and the distal end and also have an outer surface, an inner surface, and a gap defined there-between that forms a chamber. In some aspects the shaft wall can be gas permeable. The shaft may further comprise a shaft lumen open at the proximal end and distal end and bounded by the inner surface of the shaft wall. The chamber, defined between the outer surface and the inner surface of the shaft wall, may have a proximal opening connectable to a vacuum source. The proximal opening may establish vacuum communication between the chamber and the vacuum source. The chamber may also have a chamber fluid pressure therein and the chamber fluid pressure may regulatable via the vacuum source.

An additional aspect of the invention relates to a cryoablation system. The system may comprise an endoscope, a vacuum source, a sheath, and a cryoablation tool. The endoscope may have a working channel. The cryoablation tool may be of any type disclosed herein. The cryoablation tool may be extendible from and retractable within the sheath. The cryoablation tool and the sheath may be insertable in the working channel. The cryoablation tool may have a shaft and a chamber of any type disclosed herein. The shaft may be sufficiently flexible to form a curve along an extent of the chamber having a smallest radius of 20 mm. The vacuum source may be connectable to the proximal opening of the chamber for actively regulating fluid pressure in the chamber, including reducing the chamber fluid pressure.

Another aspect of the invention relates to a cryoablation system having an endoscope, a vacuum source, an insulated sheath, and a cryoablation tool. The insulated sheath may be of any type disclosed herein. The cryoablation tool may be insertable within the insulated sheath. The cryoablation tool may have a shaft and a cryogen supply conduit. The shaft may have a proximal end, a distal end, and a shaft wall. The shaft wall may extend between the proximal end and the distal end, and may have an inner surface and an outer surface, and a shaft lumen bounded by the inner surface of the shaft wall. The cryogen supply conduit may be housed within the shaft lumen and be configured to carry a cryogen from a cryogen source to a distal portion of the cryoablation tool. The cryoablation tool may be extendible from and retractable within the insulated sheath. The cryoablation tool and the sheath may be insertable in the working channel. The shaft of the cryoablation tool being sufficiently flexible to form a curve along the shaft having a smallest radius of 20 mm. The vacuum source may be connectable to the proximal opening of the chamber for actively regulating the chamber fluid pressure, including reducing the chamber fluid pressure.

The details of one or more examples are set forth in the accompanying drawings and the description below. Other features, objects, and advantages will be apparent from the description and drawings.

DETAILED DESCRIPTION

Figure 1:
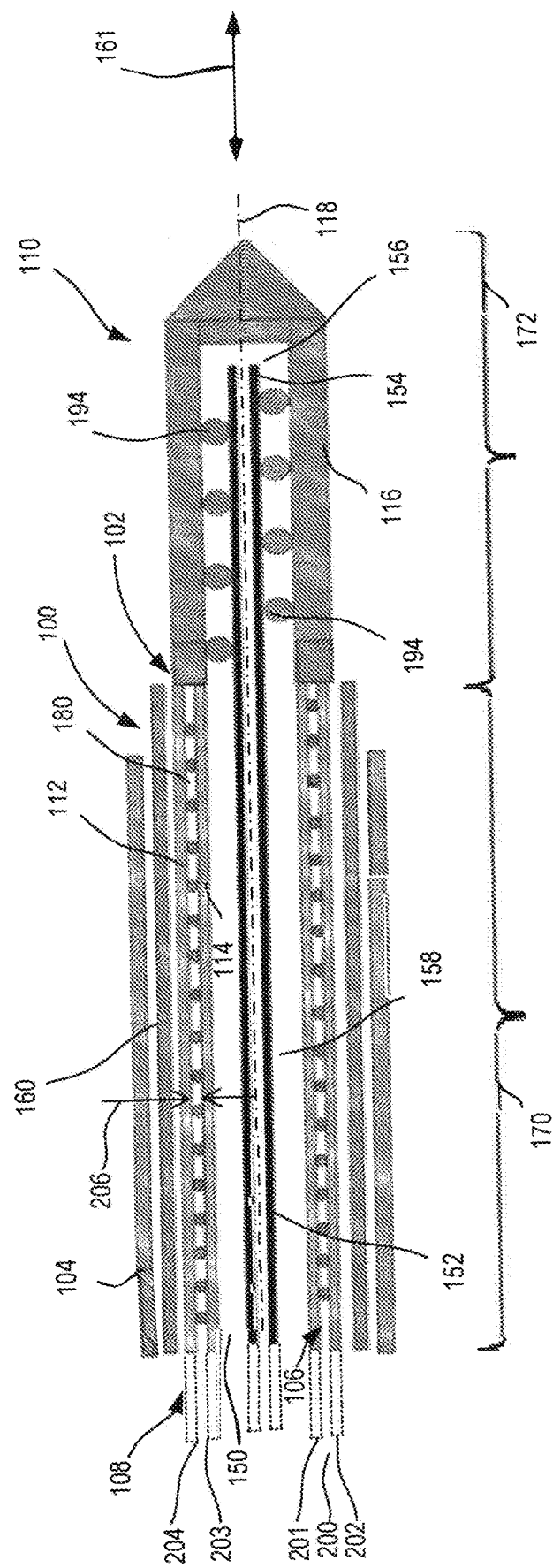
FIG. 1 is an exemplary schematic of a cryoablation system that includes a cryoablation tool according to a non-limiting exemplary embodiment.

FIG. 1 illustrates a schematic of an exemplary schematic of a cryoablation system that includes a cryoablation tool 100 according to an embodiment. According to some embodiments, the cryoablation tool 100 may include a catheter 102. In advantageous aspects, the catheter 102 may be inserted into a working channel of an endoscope such as a bronchoscope 104, and may, therefore be, generally flexible. In some aspects the cryoablation tool is used in conjunction with a sheath. The sheath may be disposed over the shaft of the tool. In some aspects the outer surface of the shaft of the cryoablation tool may be thermally insulated from the inner surface of the shaft. In some aspects, the outer surface of the shaft of the sheath is thermally insulated from the inner surface. One approach to such aspects is discussed with illustrative reference to FIG. 3A. In some aspects the cryoablation tool 100 may be part of a cryoablation system that may include a vacuum source connectible to the cryoablation tool. In some aspects the cryoablation tool 100 may be part of a cryoablation system that includes a sheath 160 and an endoscope, such as a bronchoscope 104, where the cryoablation tool is insertable into the working channel of the endoscope.

With continued reference to FIG. 1, the catheter 102 may include a tubular shaft 200 having a shaft wall 106. The shaft wall 106 may extend between a proximal end 108 and a distal end 110. The shaft wall 106 may include an outer surface 112 forming an exterior of the shaft wall 106, and an inner surface 114 forming an interior of the shaft wall 106 that defines a shaft lumen 150. In some aspects of the design, the shaft wall 106 may include an inner shaft wall 201 and may include an outer shaft wall 202. The outer surface 112 may be the outer surface of the outer shaft wall 202. The inner surface 114 may be the inner surface of the inner shaft wall 201. The outer shaft wall 202 may have an outer shaft wall inner surface 203 and the inner shaft wall 201 may have an inner shaft wall outer surface 204. A gap 206 between the outer shaft wall and the inner shaft wall forms a chamber 180, which may be annular in shape. The chamber 180 may be bounded by the outer shaft wall inner surface 203 and the inner shaft wall outer surface 204.

In one approach, the inner shaft wall 201 may be formed by an inner tubular member. The outer shaft wall 202 may likewise be formed by an outer tubular member. The outer tubular member may be radially displaced from the inner tubular member. The outer tubular member may surround the inner tubular member. A gap 206 is defined between the outer tubular member and inner tubular member. In this approach, this gap 206 forms the chamber 180.

The outer surface 112 and the inner surface 114 may each extend between the proximal end 108 and the distal end 110 of the cryoablation tool 100. Likewise, the inner shaft wall 201 and the outer shaft wall 202 may each extend between the proximal end 108 and the distal end 110 of the cryoablation tool 100. The distal end 110 of the shaft may terminate in a distal operating tip 116. The distal operating tip 116 may be surrounded by a tissue and may cryogenically ablate the tissue in some instances. The distal operating tip 116 may be advantageously configured to pierce tissue in some instances. For example, the distal operating tip 116 may include a sharp tip, such as a trocar tip. Alternatively, the distal operating tip 116 may not be a sharp tip.

In certain optional aspects referencing FIG. 1, certain portions of the shaft may be flexible. For instance, in an aspect, an entire length of the shaft extending between the proximal end 108 and the distal end 110 may be flexible. For instance, the shaft may be bendable about its longitudinal axis 118 shown by dotted lines in FIG. 1. In some such embodiments, the shaft may have a shaft diameter configured such that the shaft may be sufficiently flexible to form a curve having a desired radius of curvature. Further, in certain illustrative aspects, an entire length of the shaft may be equally flexible. In such embodiments, the curve radius of different portions of the shaft may be different.

In advantageous aspects, materials and dimensions of the shaft may be configured to provide sufficient degree of flexibility to be bendable about its longitudinal axis 118. According to an aspect, the catheter shaft may include a polymer. For instance, the inner shaft wall 201 may include a polymer. In one example, the polymer may include polyimide. In additional aspects, the outer shaft wall 202 may also include a polymer. According to one embodiment, the outer shaft wall 202 may include polyimide. Further, the outer shaft wall 202 may include polytetrafluoroethylene ("PTFE"), and/or one or more Polyether block amides (known under the tradename Pebax®, hereinafter "Pebax").

Figure 2:
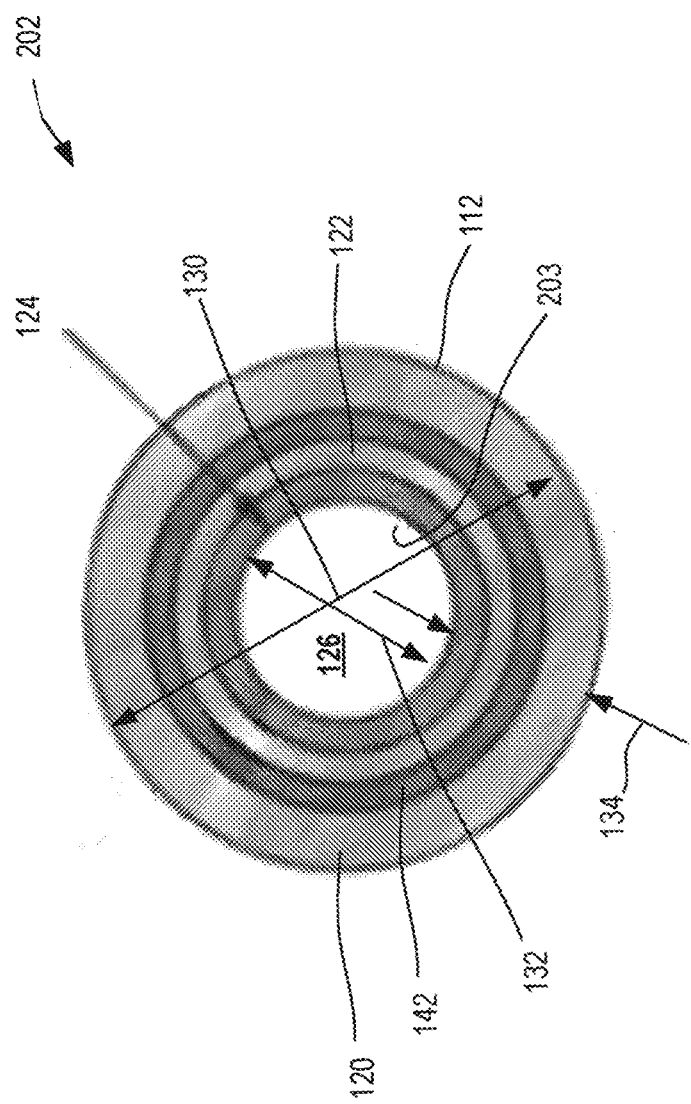
FIG. 2 is an end view of an outer tubular member with an outer surface of a shaft wall according to a non-limiting exemplary embodiment.

In one such example illustrated in FIG. 2, the outer shaft wall 202 may be formed from a generally cylindrical outer tubular member 210. In aspects of the design of the outer shaft wall, the outer surface 112 may be formed on an outer layer of the outer shaft wall 202. The outer shaft wall 202 may be formed integrally with the shaft wall 106 (FIG. 1) or it may be assembled together from separate components. The outer shaft wall 202 may include one or more layers. Accordingly, a first layer 120 of the outer shaft wall 202 may include Pebax. A second layer 122 of the outer surface 112 may include a PTFE and/or polyimide. A third layer 124 of the outer shaft wall 202 may include polyimide. The first layer 120 may be an outermost layer of the outer shaft wall. The second layer 122 may be positioned between the first layer 120 and the third layer 124. The third layer 124 may form an innermost layer of the outer shaft wall. The outer shaft wall 202 may include a hollow interior portion 126 bounded by the third layer 124 of the outer shaft wall 202 and specifically by the outer shaft wall inner surface 203.

According to an example construction, the shaft may have a shaft diameter of less than about 5 millimeters (hereinafter "mm"). Accordingly, the dimensions of the shaft wall may be configured to result in a shaft diameter of less than about 5 mm. In this example, an outer diameter 130 of the outer surface 112 (that may be formed by a tubular member) may be less than about 5 mm. In certain preferred embodiments, the outer diameter 130 of the outer surface 112 may be between about 1 mm and about 2 mm (for example, about 1.75 mm). With continued reference to FIG. 2, an inner diameter 132 of the outer shaft wall 202 may be between about 1 mm and about 1.8 mm (for example, about 1.6 mm). The outer shaft wall 202 (comprising one or more layers), may have a radial thickness 134 defined radially between the inner surface 203 and the outer surface 112. In such embodiments, the radial thickness 134 of the outer shaft wall 202 may be between about 0.01 mm and about 0.5 mm thick (e.g., about 0.07 mm).

Figure 3:
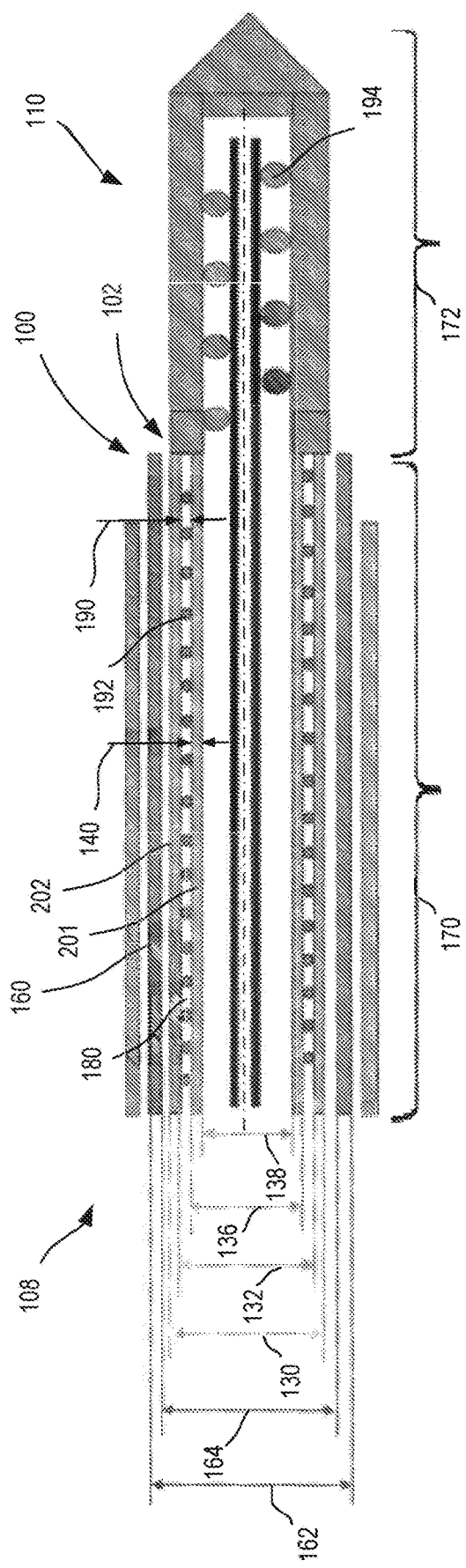
FIG. 3 is dimensioned view of the cryoablation tool of FIG. 1.

FIG. 3 illustrates a dimensioned view of the cryoablation tool 100 of FIG. 1. According to illustrative embodiments of FIG. 3, the inner shaft wall 201 of the shaft wall 106 may be formed from a generally cylindrical inner tubular member which may be a polymer tube. The inner tubular member may be inserted within the outer shaft wall 202, that may also be a generally cylindrical outer tubular member and may also be a polymer tube. In aspects of the design the inner surface 114 may be formed on an inner layer of the inner shaft wall and the outer surface 112 may be formed on an outer layer, of the outer shaft wall. The inner shaft wall 201 and the outer shaft wall 202 may be formed integrally with the shaft wall 106 or they may be assembled together from separate components In an exemplary construction, the inner shaft wall 201 may be generally coaxial with the outer shaft wall 202. The inner shaft wall 201 may have an outer diameter 136, an inner diameter 138 and a radial thickness 140 defined therebetween in the radial direction. The outer diameter 136 of the inner shaft wall may be less than the inner diameter 132 of the shaft wall 202, such that the inner shaft wall may be inserted or contained within the hollow interior of the outer shaft wall.

With reference to FIG. 3, in illustrative embodiments, the outer diameter 136 of the inner polymer may be between about 0.5 mm and about 1.5 mm (e.g., 1.4 mm). The inner diameter 138 of the inner shaft wall 201 may be between about 0.5 mm and about 1.4 mm (e.g., about 1.3 mm). The radial thickness 140 of the inner shaft wall may be about 0.01 mm and about 0.2 mm (e.g., about 0.1 mm).

In certain optional embodiments, the shaft wall 106 may include at least one reinforcement layer for mechanical strength. With reference to FIG. 2, this reinforcement layer 142 may particularly be present in the outer shaft wall 202. In the outer shaft wall, the reinforcement layer may be interposed between the first layer 120 comprising Pebax and the second layer 122 comprising polyimide. In certain examples, the reinforcement layer may include a metal (e.g., stainless steel). Further, in advantageous optional embodiments, the reinforcement layer may include a braided structure, such as a braided stainless steel.

The reinforcement layer may be generally radially outward of the inner shaft wall 201, and thus radially outward of the chamber 180, and particularly radially outward of the inner surface 203 of the outer shaft wall 202. The reinforcement layer may provide sufficient mechanical strength for withstanding pressures such as the pressure of the cryogen in the cryogen supply conduit 152 or the pressure in the cryogen return conduit 158, which functions as a shaft lumen pressure in the shaft lumen 150 defined by the inner surface 114. With reference to FIG. 2, the reinforcement layer may be generally radially outward of the second layer 122 and the third layer 124. Further, the reinforcement layer may be generally radially inward of the first layer 120.

Materials and dimensions of the shaft such as those described above may provide adequate degree of flexibility to be bendable about its longitudinal axis 118. For instance, the shaft may be sufficiently flexible, particularly along the extent of the chamber 180, such that the shaft may form a curve having a smallest radius of curvature of 20 mm, measured between a center of curvature of the bent shaft and the longitudinal axis 118. The shaft may form a curve having a smallest radius of curvature of 10 mm or even 5 mm.

Referring back to FIG. 1, according to certain aspects of the disclosure, the interior of the shaft includes a shaft lumen 150. The shaft lumen 150 may be bounded by the inner surface 114 of the shaft wall. The shaft lumen 150 may receive a cryogen. For example, in an embodiment, a cryogen supply conduit 152 may be housed (e.g., annularly) within the shaft lumen 150. The cryogen supply conduit 152 may be configured to supply a cryogen from a cryogen source to a distal portion (e.g., distal end 110 or distal operating tip 116) of the cryoablation tool 100. The cryogen supply conduit 152 may be, in some illustrative examples, a capillary tube. In optional embodiments, the cryogen supply conduit 152 may be coaxial with the shaft. The shaft lumen 150 may provide a return flow passage 158 configured to carry the cryogen gas away from the distal end of the cryoablation tool. The return flow passage 158 may be at least partially peripherally surrounded by the inner shaft wall 201, and more particularly the inner surface of the shaft 114. The return flow passage may be co-extensive with the shaft lumen 150.

In certain aspects described further below, the cryogen may pass through a cryocooler 154 and reach cryogenic temperatures. At cryogenic temperatures, the cryogen may be suitable for cooling a surface of a distal portion of the shaft. For instance, the cryogen may cool the outer surface 112 of the distal end 110 (and/or distal operating tip 116) of the shaft, and thereby remove heat (e.g., and advantageously, ablating) from tissue surrounding the distal end 110 (and/or distal operating tip 116) of the shaft.

In one arrangement, the cryogen supply conduit may terminate distally in a Joule-Thomson ("J-T") orifice 154. Accordingly, the cryocooler 154 can be an open loop cryocooler, such as the J-T orifice 154. The cryogen can be a cooling fluid (e.g., nitrogen, air, argon, krypton, xenon, $N_2O$, $CO_2$, and $CF_4$) in embodiments. In such cases, the cryogen may be at a pressure such that expansion via the J-T orifice 154 may result in the cryogen cooling to temperatures for cryogenically ablating tissue surrounding the distal operating tip 116. In certain aspects, the pressure of the cryogen upstream of the J-T orifice 154 can be between about 7 Megapascal (hereinafter, "MPa") and about 15 MPa (e.g., about 12 MPa). Accordingly, in the embodiments where the cryogen may be a cooling fluid, the temperature of the cryogen after expansion from the J-T orifice 154 can be less than about 190 Kelvin.

Alternatively, the cryogen can be a heating fluid (e.g., helium, hydrogen). In such cases, the cryogen may be at a pressure such that expansion via the J-T orifice 154 may result in a temperature increase of the cryogen, correspondingly resulting in heating of tissue surrounding the distal operating fluid. Such embodiments may be useful for thawing frozen tissue.

With continued reference to FIG. 1, in embodiments where the cryocooler 154 may be a J-T orifice 154, the distal end of the shaft may also include a distal expansion chamber 156, which may be in fluid communication with the return flow passage. The cryogen supply conduit may terminate in a J-T orifice which opens into the expansion chamber. As the cryogen leaves the cryogen supply conduit 152 via the J-T orifice 154, the cryogen may undergo J-T expansion and expand into the distal expansion chamber 156. The distal expansion chamber 156 may be disposed within the flexible portions of the shaft and may particularly be disposed within the active region 172 of the shaft and particularly within a metallic portion thereof as this improves heat exchange with tissue as explained further elsewhere herein.

Referring to FIG. 1, a cryogen return conduit 158 carry the cryogen away from the distal portion of the shaft. As illustrated, in some embodiments, the cryogen return conduit 158 may be in fluid communication with the expansion chamber. Accordingly, after expanding in the distal expansion chamber 156 the cryogen may flow via the cryogen return conduit 158. In the illustrated embodiment, the cryogen return conduit 158 may be formed by the inner surface 114 of the shaft wall 106, and may, therefore, be co-extensive with the shaft lumen 150 defined by the interior wall 114. Alternatively, the cryogen return conduit 158 may be a separate physical conduit. In an exemplary aspect, the cryogen return conduit 158 may be coaxial with the cryogen supply conduit 152. Additionally, in advantageous aspects, the cryogen return conduit 158 may annularly surround the cryogen supply conduit 152, thereby facilitating precooling (e.g., for instance, when the cryogen may be a cooling fluid) or preheating (e.g., for instance, when the cryogen may be a heating fluid) of the cryogen in the cryogen supply conduit 152 with the expanded cryogen in the cryogen return conduit 158.

Referring back to FIG. 1, the cryoablation tool 100 may include a sheath 160 which may be disposed over the shaft. The sheath 160 may, in certain embodiments, surround the shaft wall 106. For example, the sheath 160 may be disposed generally coaxially with the shaft, and may annularly surround the shaft. In advantageous aspects, the sheath 160 and the shaft wall 106 may be displaceable relative to one another. For instance, the sheath 160 and the shaft wall 106 may be displaceable as illustrated by the arrows 161 (parallel to the longitudinal axis 118) in FIG. 1. In one example, the distal portion of the shaft may be extendable beyond the sheath 160 and retractable into the sheath 160. The displacement of the sheath 160 relative to the shaft may be controllable from the proximal end 108 of the cryoablation tool 100. The sheath 160 may advantageously house and enclose the distal (e.g., sharp) operating tip of the cryoablation tool 100. Such embodiments may be advantageous, for instance, when the cryoablation tool 100 includes a sharp tip and when the cryoablation tool 100 may be inserted into the working channel of an endoscope such as a bronchoscope 104. In such instances, the sheath 160 may protect the distal (e.g., sharp) operating tip from protruding out of the sheath 160 and inadvertently damaging the working channel. Further, advantageously, the sheath 160 may protect the outer surface 112 of the shaft from mechanical damage (e.g., abrasions) when inserted into the working channel of the bronchoscope 104.

Materials of the sheath 160 may be configured to provide desired degree of flexibility and other mechanical properties. According to an aspect, the sheath 160 may include a polymer. In one embodiment, the polymer may include Pebax for sufficient flexibility and kink resistance. The polymer may also include PTFE that may offer ease of engagement of the sheath 160 with respect to the catheter 102. Additional polymer additives may be added to the materials of the sheath 160 to decrease friction on the outer surface 112 of the sheath 160. Further, optionally, the sheath 160 may be constructed as a layered arrangement of one or more polymers.

Dimensions of the sheath 160 may be configured to provide desired degree of flexibility and other mechanical properties. In an example construction, referencing FIG. 3, the sheath 160 may be sufficiently large to receive the catheter 102 there within, and yet have sufficient degree of flexibility and kink resistance. The sheath 160 may have an outer diameter 162 of between about 1 mm and about 3 mm (e.g., about 2 mm) and an inner diameter 164 of between about 1 mm and about 2 mm (e.g., about 1.8 mm).

Referring again to FIGS. 1 and 3, the shaft may include a thermally insulated region 170. When a vacuum is actively drawn in the chamber 180, at least a portion of the chamber forms a thermally insulated region that provides thermal insulation around the shaft lumen. Within the thermally insulated region 170, the surface of the shaft 112 is thermally insulated from the cryogen in the return conduit 158. The thermally insulated region may be co-extensive with the chamber 180. In the illustrated example, the thermally insulated region 170 extends for a substantial length of the shaft. The thermally insulated region 170 may thermally insulate the shaft from the sheath 160 and/or the working channel of the bronchoscope 104. Such embodiments may be advantageous in thermally insulating portions other than desired areas of the shaft from areas exterior to the shaft. For instance, the thermally insulating region may thermally insulate the shaft from portions of the patient other than a target site where a cryoablation procedure may be performed.

According to an aspect, the thermally insulated region 170 may extend over a substantial length of the shaft. In the embodiment of FIG. 3, for instance, the thermally insulated region 170 extends substantially between the proximal end 108 and distal end 110, except an active region 172 near the distal end 110. The thermally insulated region 170 may extend at least partially circumferentially around the outer diameter 136 of the inner surface 114 of the shaft. In certain advantageous aspects, the thermally insulated region 170 may provide a thermal insulation to the outer surface 112 of the shaft entirely around the diameter of the shaft.

As described previously, materials and dimensions of the shaft may be chosen so as to provide a desired degree of flexibility. Accordingly, in such embodiments, materials of the shaft wall may be gas permeable. For instance, the inner surface 114 of the shaft wall, the outer surface 112 of the shaft wall or both may be gas permeable. The inner shaft wall 201, the outer shaft wall 202 or both shaft walls may be gas permeable. The surfaces and shaft walls may be gas permeable particularly when the fluid pressure in the chamber 180 is below atmospheric pressure, such as when a partial vacuum is applied e.g. at 0.1 torr. In one arrangement, the shaft wall 106 (e.g. features such as the inner shaft wall, the outer shaft wall, the outer surface the inner surface) is configured such that, when the chamber fluid pressure is reduced to 0.1 torr, the chamber fluid pressure would increase to 0.9 torr within 30 minutes due to gas permeating through the gas permeable shaft wall, in the absence of continued evacuation.

For instance, the inner surface 114 of the shaft wall may permit expanded cryogen from the cryogen return conduit 158 to flow through the inner surface 114, and enter the annular space between the inner surface 114 and the outer surface 112 of the shaft wall. Entry of expanded cryogen may reduce thermal insulation between the inner surface 114 and the outer surface 112, thereby resulting in unintentional heat transfer between cryogen in the cryogen return conduit 158 of the shaft lumen 150 and portions of the outer surface 112 of the shaft wall and exterior areas surrounding the outer surface 112 of the shaft wall. The chamber fluid pressure being at a vacuum pressure, may lead to the cryogen gas carried in the shaft lumen 158 permeating through the shaft wall 106 into the chamber. The permeation of the cryogen through the inner shaft wall 201 may be due at least in part to shaft lumen fluid pressure being greater than the chamber 180 fluid pressure. The chamber fluid pressure will therefore increase unless the chamber fluid pressure is regulated via the vacuum source.

Optionally, the outer surface 112 of the shaft wall and or the outer shaft wall itself, may likewise be gas permeable and may permit gases from the air surrounding the shaft, such as nitrogen or oxygen, to flow through the outer surface 112, and/or the outer wall and enter the chamber 180 particularly if the fluid pressure in the chamber is less that of the air surrounding the shaft.

Gas permeating through the inner surface 114 and/or the outer surface 112 and the inner and outer shaft walls may reduce the thermal insulation capability of the shaft wall and may degrade the vacuum condition within the chamber if an active vacuum is not maintained. Accordingly, illustrative embodiments may establish an active vacuum between the inner surface 114 and the outer surface 112 of the shaft wall or the inner and outer shaft walls. For example within the chamber 180.

Figure 4:
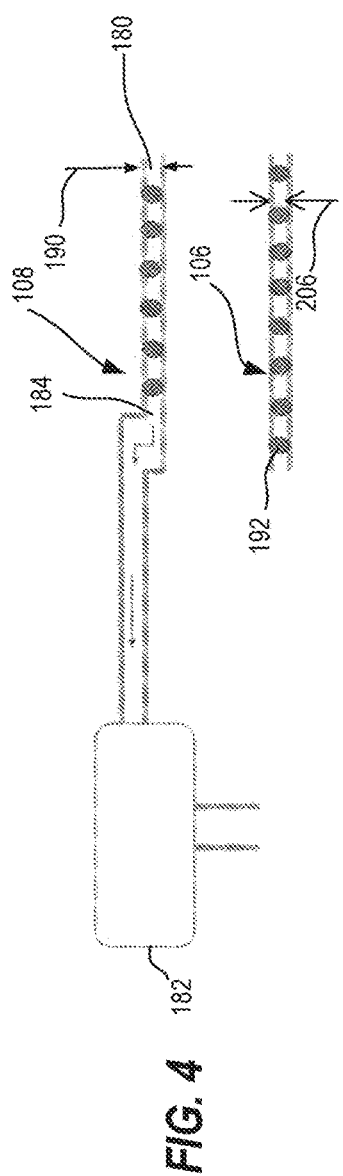
FIG. 4 is an enlarged view of a proximal end of the shaft wall along with components that may be part of a cryoablation system, an insulated sheath system, or an insulated catheter system.

FIG. 4 illustrates an enlarged view of the shaft wall. Referencing FIGS. 3 and 4, the thermally insulated region 170 may be formed by (e.g., and insulated by) a chamber 180 which may be located between the outer surface 112 and the inner surface 114. The pressure within the chamber 180, sometimes referred to as the chamber fluid pressure, may be regulatable. For example, chamber fluid pressure of the chamber 180 may be maintained at a vacuum so as to provide the thermally insulated region 170. With continued reference to FIG. 4, in certain illustrative aspects, the chamber 180 may be defined between the inner shaft outer surface 203 (e.g., radially outermost layer of the inner tubular member) and the inner surface 204 of the outer shaft 202 (e.g., radially innermost layer of the outer tubular member 112) of the shaft. The inner shaft 201 and the outer shaft 202 may be spaced apart from each other in the radial direction such that an annular gap 206 exists therebetween and forms the chamber 180. If a vacuum is applied to the chamber (as will be described further below), the chamber 180 may provide thermal insulation between the inner surface 114 of the shaft and the outer surface 112 such that the inner surface 114 is thermally insulated from the outer surface 112 and the outer surface 112 is thermally insulated from the inner surface 114.

According to aspects, the chamber 180 may at least partially circumferentially extend around the shaft lumen 150. For instance, in an embodiment, the chamber may extend entirely around the shaft lumen 150 in the circumferential direction. The chamber 180 may, as illustrated in FIG. 4, extend annularly around the shaft lumen 150 and may be coaxial therewith, in the thermally insulated region 170 of the shaft.

The cryoablation tool 100 may be configured proximally for establishing vacuum communication between the chamber 180 and a vacuum source 182. According to an embodiment illustrated in FIG. 4, the cryoablation tool 100 may be configured proximally for connection to a vacuum source 182. For instance, the chamber 180 may have a proximal opening 184 which may connect to a vacuum source 182. The opening 184 is the only opening to the chamber 180. The chamber is closed distally. In an aspect, the vacuum source 182 may be a vacuum pump 182. The vacuum pump 182 may be in operative communication with the chamber 180 (e.g., via the proximal opening 184), and may withdraw gas in the chamber 180. Except for the proximal opening 184, the chamber 180 may be sealed. If the chamber is sealed other than at the proximal opening, 184, the withdrawal of gas by the vacuum source 182 may result in the chamber fluid pressure reducing to a value below atmospheric pressure, thereby resulting in a partial vacuum. According to illustrative aspects, the partial vacuum may be actively maintained in the chamber 180. The vacuum pump 182 may continue to actively withdraw gas from the chamber 180, thereby maintaining the pressure in the chamber 180 to a value below atmospheric pressure.

The chamber 180 may have a radial thickness 190 of between about 0.01 mm and about 0.1 mm (e.g., 0.05 mm). According to an embodiment, the vacuum source 182 may maintain a chamber fluid pressure of about 0.05 torr (about 6.6 Pascals). In advantageous aspects, at such deep vacuum pressures, fluid may migrate through the inner surface 114 and/or the outer surface 112 and pass through the outer shaft and/or inner shaft into the chamber 180 due to one or more of the relatively high pressure the cryogen in the cryogen supply conduit 152, the deep vacuum in the chamber 180, a permeability of the inner surface 114, the outer surface 112, the outer shaft. The permeability of the inner surface 114 the inner shaft 201 the outer surface 112 and the outer shaft may be the result of the materials and dimensions of these features. As noted herein, in advantageous aspect of the shaft wall 106, the shaft wall 106 has an adequate degree of flexibility to be bendable about its longitudinal axis 118 in a manner as described herein. The materials (e.g., the polymers described elsewhere herein) and dimensions (the millimeter thicknesses described elsewhere herein) of the inner shaft 201 and the outer shaft 202 may be selected, in part, to provide the shaft wall 106 with such degree of flexibility. As a result, fluid (e.g., shaft lumen pressure due to expanded cryogen in the cryogen return conduit 158) may migrate into the chamber 180 due to one or more of the relatively high pressure the cryogen in the cryogen supply conduit 152, the deep vacuum in the chamber 180, the permeability of the inner shaft 201 and inner surface 114, and the permeability of the outer shaft 202 and outer surface 112. The vacuum source 182 operates actively to suction such migrated fluid out of the chamber 180 and actively maintain the chamber fluid pressure at vacuum pressures as described elsewhere herein.

With continued reference to FIG. 4, the shaft may include structures for improving mechanical strength should a vacuum be actively maintained in the chamber 180. In one embodiment, the shaft may include one or more support elements 192. The support elements 192 may, in advantageous aspects, maintain the annular spacing between the inner shaft wall 201 (which may be an inner tubular member) and the outer shaft wall 202 (which may be an outer tubular member). The support elements 192 may be disposed within the chamber. Advantageously, they may not occupy an entire volume of the chamber 180, and may partially occupy the space available in the chamber 180, which may be annular. Such embodiments may be configured to facilitate the prevention of collapse of the chamber 180 should gas be withdrawn from the chamber 180.

According to an aspect, the support elements 192 may include a supporting filament 192. The supporting filament 192 may include a polymer. In one embodiment, the polymer may include polyether ether ketone ("PEEK"). The supporting filament 192 may be formed by winding a filament, e.g. a polymer filament (e.g., PEEK) 192 in a series of turns about the inner shaft wall, more specifically about the outer face 204 of the inner shaft wall 20. According to some embodiments, the filament 192 may have a diameter between about 0.01 mm and about 0.1 mm (e.g., about 0.05 mm). The winding of a supporting filament 192 may advantageously maintain the inner shaft wall 201 in a coaxial arrangement with the outer shaft wall. The filament 192 may, advantageously prevent direct contact between the inner surface 203 of the outer shaft wall 202 (e.g. the outer tubular member) and the outer surface 204 of the inner shaft wall (e.g. the inner tubular member) and counteract the forces due to vacuum pressure and thereby improve mechanical strength of the catheter 102.

In advantageous embodiments, returning to FIG. 1, the distal end 110 of the catheter shaft may include an active region 172, over which the expanded cryogen may exchange heat with regions exterior to the shaft (e.g., tissue). The active region 172 may, accordingly, not have thermal insulation. The thermally insulated region 170 may extended over a substantial length of the catheter shaft except at the active region 172. The active region 172 may include a metallic portion disposed distally of the thermally insulated region 170. The active region 172 may facilitate heat exchange between the expanded cryogen flowing in the cryogen return conduit 158 and regions exterior to the shaft (e.g., tissue).

In accordance with certain aspects of the present disclosure, the active region 172 may also be substantially flexible. The active region 172 may be flexible substantially to the same degree as the thermally insulated region 170. The active region 172 may be include one or more bellows, grooves, and the like, and may offer satisfactory degree of bendability without kinking within the metallic region. The shaft may thus comprise a flexible metallic region, disposed at the distal end 110 of the shaft 200. The flexible metallic region may terminate in a distal tip operating tip 116 which may be configured for penetration of tissue.

Referring back to FIGS. 1 and 3, according to certain embodiments, the catheter 102 may include a heat-exchange spiral 194 wound around at least distally over the cryogen supply conduit 152. The heat-exchange spring 194 may enhance circulation and/or residence time of the cryogen (e.g., upon expansion) and may, additionally help maintain the coaxial arrangement between the cryogen supply conduit 152 and the active metal region. In an embodiment, the heat-exchange spiral 194 may be formed from a metallic (e.g. tin-coated copper) wire wound around the distal end 110 of the cryogen supply conduit 152 (e.g., capillary tube). The heat-exchange spiral 194 may have a desired pitch (e.g., between about 1 mm and about 10 mm, for instance, about 4 mm).

In a further embodiment, the shaft walls of the thermally insulated region of the cryoablation tool may be used as the shaft wall of an insulated sheath, or may be further used as the shaft walls of an insulated catheter. The insulated sheath may be used with a cryoablation tool as described further herein.

Cryoablation tools may lack a thermally insulated region, but may never the less be used in conjunction with an endoscope, such as a bronchoscope or similar device. In one approach, cryoablation tools may be used in conjunction with an insulated sheath in order to provide protection for the working channel of an endoscope from the cryogenic temperatures that may be found in the cryoablation tool. The sheath may also provide protection for tissue that is not intended to be ablated.

Figure 3A:
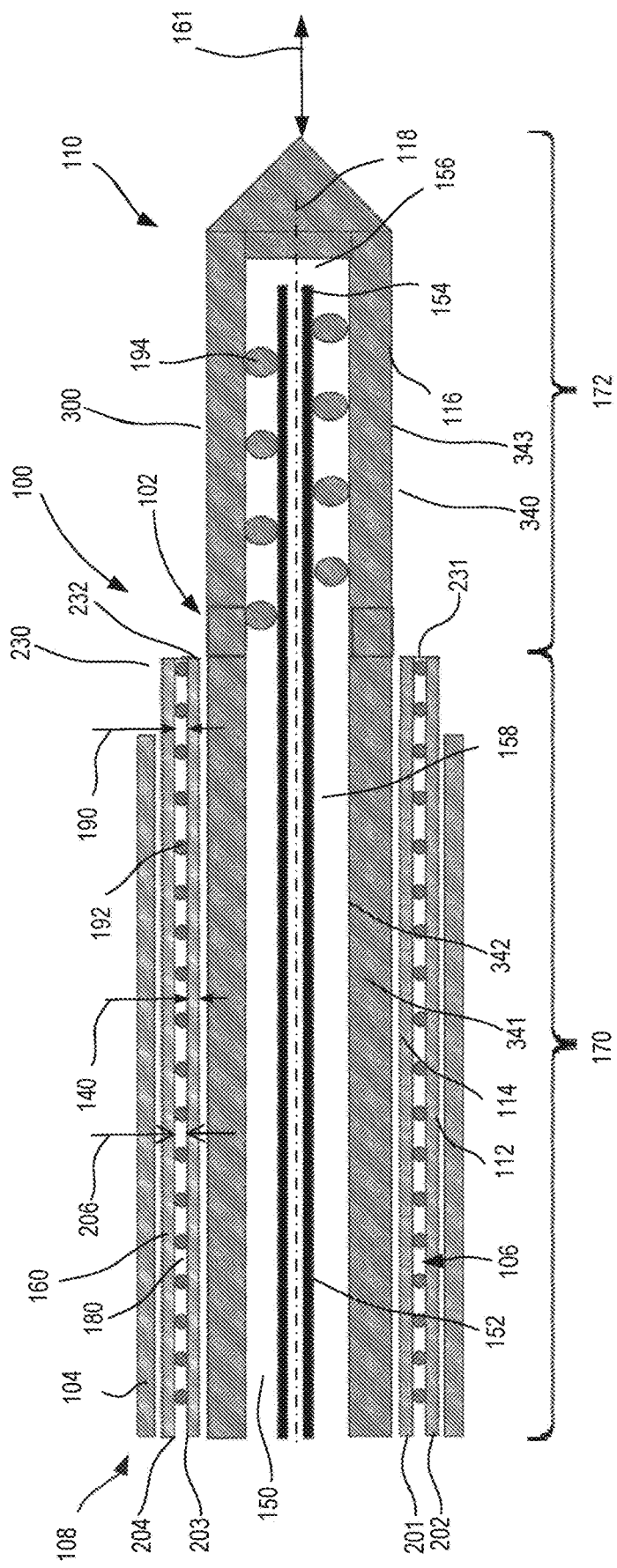
FIG. 3A is an exemplary schematic of a system that includes an insulated sheath according to a non-limiting exemplary embodiment.

With reference to FIG. 3A a sheath (or catheter) has a shaft wall 106, which is generally tubular and has a proximal end 108 and a distal end 230. The shaft is provided with the same features as the shaft of cryoablation tools described elsewhere herein.

A shaft wall 106 extends between the proximal end and the distal end. The shaft wall has an outer surface 112 and an inner surface 114. A gap 206 may be defined between the outer surface of the shaft 112 and the inner surface of the shaft 114. This gap 206 may define a chamber 180 between the two surfaces. The chamber may be sealed at the distal end 230 such as by a closure 231.

The shaft may comprise an inner shaft wall 201 and may also comprise an outer shaft wall 202. The outer surface of the outer shaft wall 202 may provide the outer surface 112 of the shaft. The inner surface of the inner shaft wall 201 may provide the inner surface 114 of the shaft. The chamber 180 may be defined between outer shaft wall 202 and the inner shaft wall 201. More specifically the chamber 180 may be defined between the outer shaft wall inner surface 203 and the inner shaft wall outer surface 204.

The components, construction, materials and gas permeability properties of the shaft wall are as per those of the cryoablation tool described in detail elsewhere herein.

The sheath or catheter has a shaft lumen 232 bounded by the inner surface of the shaft wall 114, the shaft lumen of a sheath may be configured for receiving a cryoablation tool 300, The lumen of a sheath or catheter may be open at the distal end 230 and may be open at the proximal end. With reference to FIG. 4 and analogously, the chamber defined between the inner surface 114 and outer surface 112 of the shaft may have a proximal opening 184 connectable to a vacuum source 182, the proximal opening 184 being configured to establish vacuum communication between the chamber 180 and the vacuum source, the chamber having a chamber fluid pressure therein. Connection of the chamber 180 to the vacuum source 182 allows the chamber fluid pressure to be regulated by the vacuum source analogously to the approach discussed elsewhere herein in relation to a cryoablation tool.

With continued reference to FIG. 3a, a cryoablation tool 300 has a shaft 340 having 108 and a distal end 110. A shaft wall 341 extends between the proximal end and 108 and the distal end 110. The shaft wall having an inner surface 342 and an outer surface 343. The shaft wall is typically of a polymeric nature and may in some approaches, be constructed of a series of layers in the same manner as the outer shaft wall of cryoablation tools described elsewhere herein and with reference to FIG. 2. In particular the shaft wall may comprise a reinforcing layer 142, which may comprise a braided layer, particularly a stainless steel braid as described elsewhere herein. The tool may have a shaft lumen 158 bounded by the inner surface 342 of the shaft wall. A cryogen supply conduit 152 may be housed within the shaft lumen, the cryogen supply conduit configured to carry a cryogen from a cryogen source to a distal portion 110 of the cryoablation tool. The tool may be provided with a cryogen return passage for evacuation of the cryogen, which, as for the devices discussed elsewhere herein, typically evacuates proximally or may be recycled. The return flow passageway may be provided by the shaft lumen, which may be configured to carry the cryogen gas away from the distal end of the cryoablation tool.

The distal end 110 of the cryoablation tool may terminate in a distal operating tip 116. The distal operating tip 116 may be advantageously configured to pierce tissue. For example, the distal operating tip 116 may include a sharp tip, such as a trocar tip. Alternatively, the distal operating tip 116 may not be a sharp tip.

In one arrangement, the cryogen supply conduit may terminate distally in a Joule-Thomson ("J-T") orifice 154. The distal end of the shaft may also include a distal expansion chamber 156, which may be in fluid communication with the return flow passage. The cryogen supply conduit may terminate in a J-T orifice which opens into the expansion chamber.

Illustrative Examples

Figure 5:
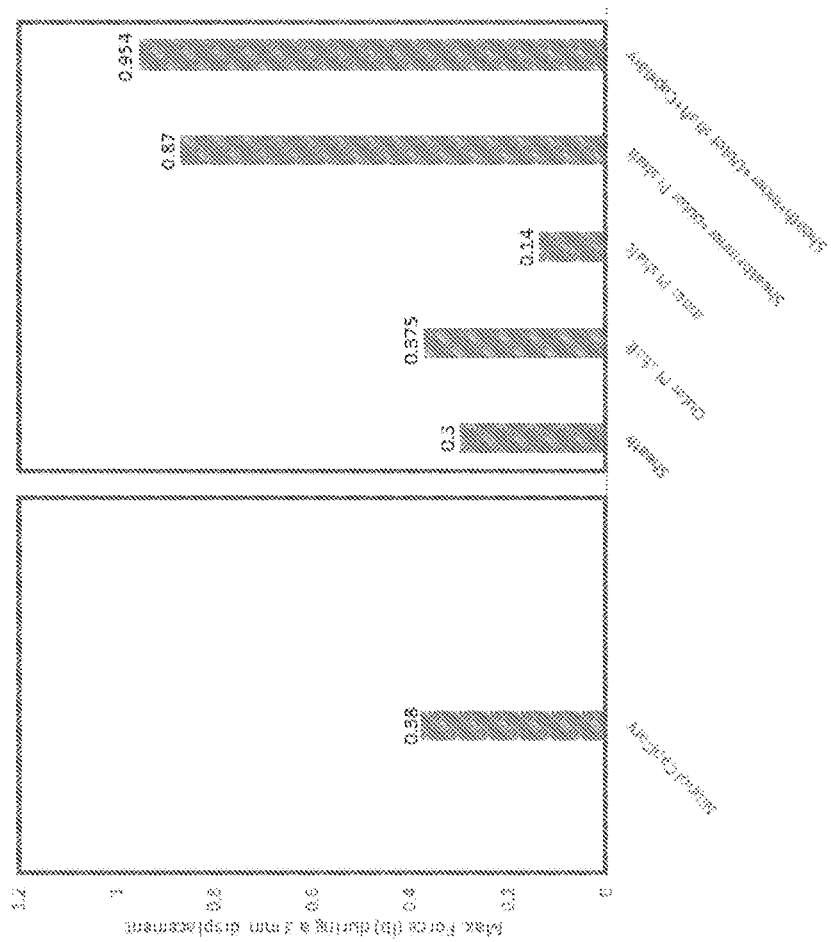
FIG. 5 is a plot illustrating the details of a three-point bend test of components of an illustrative cryoablation tool.

FIG. 5 illustrates the flexibility of various components of the catheter 102 according to an embodiment. The flexibility of the components may be quantified by a three-point bend test. The tested components were supported between two points at a distance of about 25 mm apart. The force (in pounds) required to deflect the tested component by about 3 mm is plotted in FIG. 5.

With continued reference to FIG. 5, in an embodiment, the outer shaft wall 202 is constructed to have an inner diameter 132 of about 1.6 mm, an outer diameter 130 of about 1.75 mm, a first layer 120 comprising Pebax® 72D, a reinforcement layer 142 having a stainless steel wire braiding, a second layer 122 comprising a polyimide-PTFE blend, and a third layer 124 comprising polyimide. The force for deflecting the outer surface 112 by 3 mm is about 0.375 pounds (about 1.668 N). The outer shaft wall 202 according to this embodiment may have a bend radius of about 12.7 mm and a burst pressure of about 27 MPa.

Referencing FIG. 5, in another embodiment, the inner shaft wall 201 is constructed to have an inner diameter 138 of about 1.32 mm, an outer diameter 136 of about 1.45 mm, and includes polyimide. The force for deflecting the inner shaft wall 201 by about 3 mm is about 0.14 pounds (about 0.6228 N).

Referring again to FIG. 5, in another embodiment, the sheath 160 is constructed to have an inner diameter 164 of 1.8 mm and an outer diameter 162 of about 2 mm. The sheath 160 includes a plurality of layers, with a first layer 120 of the sheath 160 including PTFE, a second layer 122 of the sheath 160 including stainless steel, a third layer 124 of the sheath 160 including Pebax 63D®. The bend radius of the sheath 160 was about 12.7 mm. The force for deflecting the sheath 160 by about 3 mm is about 0.3 pounds (about 1.334 N).

In a further embodiment, the cryogen supply conduit 152 includes a nitinol capillary tube having an outer diameter of about 0.57 mm. According to this embodiment, the force for deflecting the capillary tube by 3 mm is about 0.38 pounds (about 1.69 N). The combined force for deflecting the sheath 160, the outer surface 112, the inner surface 114, and the capillary tube by about 3 mm may be about 0.954 pounds (about 4.244 N).

A further embodiment provides an insulated sheath. The insulated sheath may be used with a cryoablation tool as described further herein, or it may be adapted as an insulated catheter.

Cryoablation tools may lack a thermally insulated region, but may never the less be used in conjunction with an endoscope, such as a bronchoscope or similar device. In one approach, cryoablation tools may be used in conjunction with an insulated sheath in order to provide protection for the working channel of an endoscope from the cryogenic temperatures that may be found in the cryoablation tool. The sheath may also provide protection for tissue that is not intended to be ablated.

With reference to FIG. 3A a sheath or catheter has a shaft wall 106, which is generally tubular and has a proximal end 108 and a distal end 230. The shaft is provided with the same features as the shaft of cryoablation tools described elsewhere herein.

A shaft wall 106 extends between the proximal end and the distal end. The shaft wall 106 has an outer surface 112 and an inner surface 114. A gap 206 may be defined between the outer surface of the shaft 112 and the inner surface of the shaft 114. This gap 206 may define a chamber 180 between the two surfaces. The chamber may be sealed at the distal end 230 such as by a closure 231.

The shaft may comprise an inner shaft wall 201 and may also comprise an outer shaft wall 202. The outer surface of the outer shaft wall 202 may provide the outer surface 112 of the shaft. The inner surface of the inner shaft wall 201 may provide the inner surface 114 of the shaft. The chamber 180 may be defined between outer shaft wall 202 and the inner shaft wall 201. More specifically the chamber 180 may be defined between the outer shaft wall inner surface 203 and the inner shaft wall outer surface 204.

The components, construction, materials and gas permeability properties of the shaft wall are as per those of the cryoablation tool described in detail elsewhere herein.

The sheath or catheter has a shaft lumen 232 bounded by the inner surface of the shaft wall 114, the shaft lumen of a sheath may be configured for receiving a cryoablation tool 300, The lumen of a sheath or catheter may be open at the distal end 230 and may be open at the proximal end. With reference to FIG. 4 and analogously, the chamber defined between the inner surface 114 and outer surface 112 of the shaft may have a proximal opening 184 connectable to a vacuum source 182, the proximal opening 184 being configured to establish vacuum communication between the chamber 180 and the vacuum source, the chamber having a chamber fluid pressure therein. Connection of the chamber 180 to the vacuum source 182 allows the chamber fluid pressure to be regulated by the vacuum source analogously to the approach discussed elsewhere herein in relation to a cryoablation tool.

With continued reference to FIG. 3A, a cryoablation tool 300 has a shaft 340 having 108 and a distal end 110. A shaft wall 341 extends between the proximal end and 108 and the distal end 110. The shaft wall having an inner surface 342 and an outer surface 343. The shaft wall is typically of a polymeric nature and may in some approaches, be constructed of a series of layers in the same manner as the outer shaft wall of cryoablation tools described elsewhere herein and with reference to FIG. 2. In particular the shaft wall may comprise a reinforcing layer 142, which may comprise a braided layer, particularly a stainless steel braid as described elsewhere herein. The tool may have a shaft lumen 158 bounded by the inner surface 342 of the shaft wall. A cryogen supply conduit 152 may be housed within the shaft lumen, the cryogen supply conduit configured to carry a cryogen from a cryogen source to a distal portion 110 of the cryoablation tool. The tool may be provided with a cryogen return passage for evacuation of the cryogen, which, as for the devices discussed elsewhere herein, typically evacuates proximally or may be recycled. The return flow passageway may be provided by the shaft lumen, which may be configured to carry the cryogen gas away from the distal end of the cryoablation tool.

The distal end 110 of the cryoablation tool may terminate in a distal operating tip 116. The distal operating tip 116 may be advantageously configured to pierce tissue. For example, the distal operating tip 116 may include a sharp tip, such as a trocar tip. Alternatively, the distal operating tip 116 may not be a sharp tip.

In one arrangement, the cryogen supply conduit may terminate distally in a Joule-Thomson ("J-T") orifice 154. The distal end of the shaft may also include a distal expansion chamber 156, which may be in fluid communication with the return flow passage. The cryogen supply conduit may terminate in a J-T orifice which opens into the expansion chamber.

We claim:

1. A cryoablation tool, comprising:
   a shaft having:
   a proximal end,
   a distal end,
   a shaft wall extending between the proximal end and the distal end, the shaft wall having an outer surface and an inner surface and a gap defined therebetween that forms a chamber, the shaft wall being gas permeable,
   a shaft lumen open at the proximal end and the distal end and bounded by the inner surface of the shaft wall; and
   wherein the chamber sealed at the distal and comprises a proximal opening connectable to a vacuum source, wherein the proximal opening establishes vacuum communication between the chamber and the vacuum source, and
   the chamber has a chamber fluid pressure therein, the chamber fluid pressure being regulatable via the vacuum source that is configured to actively maintain the chamber fluid pressure at vacuum pressures such that a shaft lumen fluid pressure is greater than the chamber fluid pressure; and
   wherein the gas permeable shaft wall is configured such that a cryogen carried in the shaft lumen is configured to permeate through the inner surface of the shaft wall into the chamber when the shaft lumen fluid pressure is greater than the chamber fluid pressure.

2. The cryoablation tool of claim 1, wherein the shaft wall comprises an inner shaft wall and an outer shaft wall, wherein the inner surface is the inner surface of the inner shaft wall and the outer surface is the outer surface of the outer shaft wall and wherein a gap defined between the outer shaft wall and the inner shaft wall forms the chamber.

3. The cryoablation tool of claim 2, wherein the inner shaft wall is formed by an inner tubular member and the outer shaft wall is formed by an outer tubular member, wherein the outer tubular member surrounds the inner tubular member, and wherein the gap is defined between the outer tubular member and inner tubular member to form the chamber.

4. The cryoablation tool of claim 1, wherein the gas permeable shaft wall is configured such that, gases from the air surrounding the outside of the shaft permeates through the shaft wall into the chamber to increase the chamber fluid pressure unless the chamber fluid pressure is regulated via the vacuum source.

5. The cryoablation tool of claim 1, comprising one or more support elements configured to prevent collapse of the chamber when gas is withdrawn from the chamber.

6. The cryoablation tool of claim 1, wherein when a vacuum is actively drawn in the chamber, at least a portion of the chamber forms a thermally insulated region that provides thermal insulation around the shaft lumen.

7. The cryoablation tool of claim 1, further comprising a cryogen supply conduit housed within the shaft lumen, the cryogen supply conduit configured to carry a cryogen from a cryogen source to a distal portion of the cryoablation tool and terminating in a Joule-Thomson orifice that opens into a distal expansion chamber of the shaft lumen so as to form an open loop cryogen supply system.

8. The cryoablation tool of claim 7, wherein the cryogen carried in the shaft lumen permeating through the inner surface of the shaft wall into the chamber when the shaft lumen fluid pressure is greater than the chamber fluid pressure causes the chamber fluid pressure to increase towards the shaft lumen fluid pressure over time, unless the chamber fluid pressure is regulated via the vacuum source.

9. A cryoablation system, comprising:
   an endoscope having a working channel;
   a vacuum source that is configured to actively maintain a chamber fluid pressure at vacuum pressures such that a shaft lumen fluid pressure is greater than the chamber fluid pressure; and
   a cryoablation tool insertable in the working channel comprising,
   a shaft having:
   a proximal end,
   a distal end,
   a shaft wall extending between the proximal end and the distal end, the shaft wall having an outer surface and an inner surface and a gap defined therebetween that forms a chamber, the shaft wall being gas permeable,
   a shaft lumen bounded by the inner surface of the shaft wall, wherein
   the chamber has a proximal opening connectable to the vacuum source, the proximal opening establishes vacuum communication between the chamber and the vacuum source, and
   the chamber is at the chamber fluid pressure therein, the chamber fluid pressure being regulatable via the vacuum source; and
   wherein the gas permeable shaft wall is configured such that the cryogen carried in the shaft lumen is configured to permeate through the inner surface of the shaft wall into the chamber when the shaft lumen fluid pressure is greater than the chamber fluid pressure.

10. The cryoablation system of claim 9, wherein a fluid pressure of the shaft lumen due to expanded cryogen in the shaft lumen is greater than the chamber fluid pressure due to the vacuum source such that the chamber fluid pressure is increased unless the chamber fluid pressure is regulated via the vacuum source.

11. The cryoablation system of claim 9, wherein the chamber fluid pressure is regulatable from a high pressure at the cryogen supply conduit to a deep vacuum at the chamber via the vacuum source.

12. The cryoablation system of claim 11, wherein the shaft wall is fluid permeable when the chamber fluid pressure is at deep vacuum pressures such that fluid is allowed to migrate into the chamber, and the vacuum source is configured to operate to actively suction migrated fluid out of the chamber while actively maintaining the chamber fluid pressure at the vacuum pressures.

13. The cryoablation system of claim 9, wherein the chamber is sealed other than at the proximal opening such that withdrawal of cryogen by the vacuum source reduces the chamber fluid pressure to a value below atmospheric pressure to thereby establish a partial vacuum.

14. A cryoablation tool, comprising:
a shaft having:
a proximal end,
a distal end,
a shaft wall extending between the proximal end and the distal end, the shaft wall having an outer surface and an inner surface and a gap defined therebetween that forms a chamber, the shaft wall being gas permeable,
a shaft lumen bounded by the inner surface of the shaft wall, and
a cryogen supply conduit housed within the shaft lumen, the cryogen supply conduit configured to carry a cryogen from a cryogen source to a distal portion of the cryoablation tool, wherein
the shaft lumen provides a return flow passage configured to carry the cryogen away from the distal end of the cryoablation tool,
the chamber has a proximal opening connectable to a vacuum source, the proximal opening establishes vacuum communication between the chamber and the vacuum source, and
the chamber has a chamber fluid pressure therein, the chamber fluid pressure being regulatable from a high pressure at the cryogen supply conduit to a deep vacuum at the chamber via the vacuum source that is configured to actively maintain the chamber fluid pressure at vacuum pressures such that a shaft lumen fluid pressure is greater than the chamber fluid pressure,
wherein a portion of the shaft wall includes polyimide; and
wherein the gas permeable shaft wall is configured such that the cryogen carried in the return flow passage of the shaft lumen is configured to permeate through the inner surface of the shaft wall into the chamber when the shaft lumen fluid pressure is greater than the chamber fluid pressure, causing the chamber fluid pressure to increase towards the shaft lumen fluid pressure over time, unless the chamber fluid pressure is regulated via the vacuum source.

15. The cryoablation tool of claim 14, wherein the outer surface of the shaft wall is a multilayered material comprising a first layer and a second layer, wherein the first layer is different from the second layer.

16. The cryoablation tool of claim 15, wherein the first layer includes one or more Polyether block amides, and wherein the second layer includes polyimide.

17. The cryoablation tool of claim 16, further comprising a third layer, wherein the first layer is an outermost layer of the outer surface, and wherein the second layer is positioned between the first layer and the third layer such that the third layer is an innermost layer of the outer surface, wherein the third layer includes at least one of polytetrafluoroethylene and polyimide.

18. The cryoablation tool of claim 14, wherein fluid is allowed to migrate into the chamber due to one or more of the high pressure at the cryogen supply conduit, the deep vacuum in the chamber, a permeability of the inner surface, and a permeability of the outer surface.

19. The cryoablation tool of claim 14, wherein the high pressure is between 7 megapascal and 15 megapascal, and the chamber fluid pressure is between 0.01 torr and 0.05 torr.

20. The cryoablation tool of claim 14, wherein the cryogen carried in the return flow passage of the shaft lumen permeating through the inner surface of the shaft wall into the chamber when the shaft lumen fluid pressure is greater than the chamber fluid pressure causes the chamber fluid pressure to increase towards the shaft lumen fluid pressure over time, unless the chamber fluid pressure is regulated via the vacuum source.

* * * * *